(12) United States Patent
Rubin

(10) Patent No.: US 10,251,836 B2
(45) Date of Patent: Apr. 9, 2019

(54) TREATMENT OF ENDOMETRIOSIS BY INTRAVAGINAL ADMINISTRATION OF A LOW DOSE OF A SELECTIVE PROGESTERONE RECEPTOR MODULATOR (SPRM), ANTI-PROGESTIN, OR ANTI-PROGESTATIONAL AGENT

(71) Applicant: ARSTAT Inc., Flemington, NJ (US)

(72) Inventor: Arkady Rubin, Flemington, NJ (US)

(73) Assignee: Arstat, Inc., Flemington, NJ (US)

(*) Notice: Subject to any disclaimer, the term of this patent is extended or adjusted under 35 U.S.C. 154(b) by 0 days.

(21) Appl. No.: 14/017,530

(22) Filed: Sep. 4, 2013

(65) Prior Publication Data

US 2014/0004171 A1 Jan. 2, 2014

Related U.S. Application Data

(63) Continuation of application No. PCT/US2011/066548, filed on Dec. 21, 2011.

(60) Provisional application No. 61/451,459, filed on Mar. 10, 2011.

(51) Int. Cl.
| | |
|---|---|
| *A61K 31/569* | (2006.01) |
| *A61P 15/02* | (2006.01) |
| *A61K 9/00* | (2006.01) |
| *A61K 31/575* | (2006.01) |
| *A61K 31/57* | (2006.01) |

(52) U.S. Cl.
CPC .......... *A61K 9/0036* (2013.01); *A61K 9/0039* (2013.01); *A61K 31/569* (2013.01); *A61K 31/57* (2013.01); *A61K 31/575* (2013.01); *A61P 15/02* (2018.01)

(58) Field of Classification Search
CPC .... A61K 9/0036; A61K 31/57; A61K 31/569; A61K 31/575; A61P 15/02
See application file for complete search history.

(56) References Cited

U.S. PATENT DOCUMENTS

| | | |
|---|---|---|
| 5,188,835 A | 2/1993 | Lindskog et al. |
| 2005/0197651 A1* | 9/2005 | Chen et al. ................ 604/890.1 |
| 2007/0213306 A1 | 9/2007 | Hausknecht |
| 2010/0087402 A1 | 4/2010 | Wang et al. |

OTHER PUBLICATIONS

"Emerging drugs for endometriosis" by Fedele et al., Expert Opin. Emerg. Drugs 9(1), 167-77 (2004).*
Eisinger SH, Fiscella J, Bonfiglio T, Meldrum S, Fiscella K. Open-label study of ultra low-dose mifepristone for the treatment of uterine leiomyomata. Eur J Obstet Gynecol Reprod Biol. Oct. 2009; 146(2): 215-8. PubMed PMID: 19586708. (Year: 2009).*
Carbonell JL, Acosta R, Pérez Y, Garcés R, Sánchez C, Tomasi G. Treatment of Uterine Myoma with 2.5 or 5 mg Mifepristone Daily during 3 Months with 9 Months Posttreatment Followup: Randomized Clinical Trial. ISRN Obstet Gynecol. Jul. 29, 2013; 2013: 649030. PubMed PMID: PMC3747426. (Year: 2013).*
Philip B. Clement; "The Pathology of Endometriosis: A Survey of the Many Faces of a Common Disease Emphasizing Diagnostic Pitfalls and Unusual and Newly Appreciated Aspects"; Jul. 2007; pp. 241-260; Adv Anat Pathol; vol. 14; No. 4; Vancouver, BC, Canada.
Abbott Laboratories, "Lupron Depot: Understanding Endometriosis"; accessed online Dec. 14, 2011 at http://www.endofacts.com/undertsanding-endometriosis.cfm.
Janos Garai et al.; "Endometriosis: Harmful Survival of an Ectopic Tissue"; Jan. 1, 2006; Frontiers in Bioscience 1; pp. 595-619.
American Society for Reproductive Medicine; "Endometriosis: A Guide for Patients"; Patient Information Series, American Society for Reproductive Medicine; 2007; Birmingham, Alabama.
Ari Babaknia; "Endometriosis: The '90s Outlook"; Endometriosis FAQ; accessed online Oct. 29, 2010 at http://www.bioscience.org/books/endomet/end01-33.htm.
Abstract; Luigi Fedele et al.; "Emerging Drugs for Endometriosis"; Expert Opinion on Emerging Drugs, Informa Healthcare; May 2004; vol. 9; No. 1; pp. 167-177; Milan, Italy; accessed online Aug. 19, 2013 at http://informahealthcare.com/doi/abs/10.1517/14728214.9.1.167.
Irving M. Spitz, "Mifepristone: where do we come from and where are we going? Clinical development over a quarter of a century"; Contraception (2010) Dec. 12, 2009; Jerusalem, Israel.
Natalie Chabbert-Buffet, et al.; "Selective Progesterone Receptor Modulators and Progesterone Antagonists: Mechanisms of Action and Clinical Applications"; Mar. 24, 2004; Human Reproduction Update; vol. 11; No. 3; pp. 293-307.
Jody Steinauer et al., "Systematic Review of Mifepristone for the Treatment of Uterine Leiomyomata"; vol. 103, No. 6, Jun. 2004, Obstetrics & Gynecology; pp. 1331-1336.
Irving M. Spitz, "Pharmacology and mechanisms of action of progesterone receptor antagonists and selective progesterone receptor modulators"; UpToDate.Online 18.2; accessed online Aug. 22, 2010 at http://www.uptodate.com/online/content/topic.do?topicKey=r_endo_f/23818&selectedTitle=1%7E81&source=search_result.
Wikipedia, "Mifepristone"; accessed online Dec. 1, 2011 at http://en.wikipedia.org/wiki/Mifepristone.
S.H. Eisinger et al., "Twelve-month safety and efficacy of low-dose mifepristone for uterine myomas"; J Minim Invasive Gynecol May-Jun. 2005; 12(3): 227-33; accessed online Jun. 4, 2010 at http://www.ncbi.nlm.nih.gov/pubmed/15922980?dopt=Abstract.
Mediterranea Medica Clinic et al., "3rd Symposium on Misoprostol and Mifepristone in Gynecology and Obstetrics"; [meeting abstract] Oct. 4-5, 2007; Valencia, Spain.

(Continued)

*Primary Examiner* — Theodore R. West
(74) *Attorney, Agent, or Firm* — M&B IP Analysts, LLC

(57) ABSTRACT

A method and intravaginal drug delivery device for reducing size of endometrial implants in a female in need thereof are provided. The method includes administering intravaginally to the female a therapeutically effective amount of an active agent, wherein the agent is delivered on a delivery device directly to the endometrial implants, wherein said amount is able to significantly reduce the size of endometrial implants, wherein the active agent is any one of selective progesterone receptor modulator (SPRM), an anti-progestin agent, and an anti-progestational agent.

8 Claims, No Drawings

(56) References Cited

OTHER PUBLICATIONS

Kevin Fiscella et al., "Effect of Mifepristone for Symptomatic Leiomyomata on Quality of Life and Uterine Size: A Randomized Controlled Trial"; vol. 108, No. 6, Dec. 2006; Obstetrics and Gynecology; pp. 1381-1387.
Josep Lluis Carbonell Esteve et al., "Mifepristone for the Treatment of Uterine Leiomyomas: A Randomized Controlled Trial"; vol. 112, No. 5, Nov. 2008; Obstetrics and Gynecology; pp. 1029-1036.
Steve H. Eisinger et al., "Open-label study of ultra low-dose mifepristone for the treatment of uterine leiomyomata"; European Journal of Obstetrics & Gynecology and Reproductive Biology 146 (2009) 2009; pp. 215-218.
Abstract; LM Kettel; "Endocrine responses to long-term administration of the antiprogesterone RU486 in patients with pelvic endometriosis"; Sep. 1991; Fertil Steril 1991; vol. 56; No. 3; accessed online Aug. 19, 2013 at http://www.ncbi.nlm.nih.gov/pubmed/1716596.
Summary; Molla S. Donaldson et al.; "Clinical Applications of Mifepristone (RU486) and Other Antiprogestins: Assessing the Science and Recommending a Research Agenda" National Academy of Sciences 1993; National Academy Press; Washington, D.C.
Abstract; LM Kettel et al.; "Treatment of endometriosis with the antiprogesterone mifepristone (RU486)"; Jan. 1996; Fertil Steril 1996; vol. 65; No. 1; pp. 23-28; accessed online Aug. 19, 2013 at http://www.ncbi.nlm.nih.gov/pubmed/8557150.
L. Michael Kettel et al.; "Preliminary report on the treatment of endometriosis with low-dose mifepristone (RU 486)"; Jun. 1998; Am J Obstet Gynecol; vol. 178; No. 6; pp. 1151-1156; La Jolla, California.
Hong-Yuan Huang; "Medical Treatment of Endometriosis"; Chang Gung Med J 2008; vol. 31; pp. 431-440; Taoyuan, Taiwan.
Kevin Fiscella, "Use of Antiprogestons for Treatment of Uterine Fibroids: Clinical Trials"; [presentation]; Advances in Uterine Leiomyoma Research, 2nd NIH International Congress, Feb. 24-25, 2005; Bethesda MD.
SA Kingsberg et al., "Treating dyspareunia caused by vaginal atrophy: a review of treatment options using vaginal estrogen therapy"; International Journal of Women's Health 2009; Aug. 20, 2009; vol. 1, pp. 105-111.
Susan A. Ballagh, "Vaginal Ring Hormone Delivery Systems in Contraception and Menopause"; Clinical Obstetrics and Gynecology, Mar. 2001; vol. 44, No. 1, pp. 106-113.
Vidya Iyer et al., "Vaginal drug delivery"; Express Pharma; accessed online Jul. 15, 2008 at http://pharma.financialexpress.com/20080715/research02.shtml.
Masao Igarashi et al., "Novel vaginal danazol ring therapy for pelvic endometriosis, in particular deeply infiltrating endometriosis"; Human Reproduction 1998; vol. 13, No. 7, pp. 1952-1956.
Abstract: C.C. Ficicioglu et al., "High local endometrial effect of vaginal progesterone gel"; Gynecological Endocrinology, vol. 18, Issue 5, May 2004, pp. 240-243; accessed online Mar. 14, 2012 at http://pubget.com/paper/15346659?cb=1331781481.
H. Kuhl, "Pharmacology of estrogens and progestogens: influence of different routes of administration"; Climacteric 2005; vol. 8 (Suppl 1) pp. 3-63; Frankfurt, Germany.
Center for Drug Evaluation and Research: "Application No. 21-225 Medical Review"; completed Dec. 5, 2000; accessed online at http://www.accessdata.fda.gov/drugsatfda_docs/nda/2000/21-225.pdf_Mirena_Medr.pdf.
Abstract; C.G. Nilsson et al.; "Tissue Concentrations of Levonorgetrel in Women Using a Levonorgestrel-Releasing IUD"; Dec. 1982; Clinical Endocrinology; vol. 17; No. 6; pp. 529-536; accessed online Aug. 19, 2013 at http://onlinelibrary.wiley.com/doi/10.1111/j.1365-2265.1982.tb01625.x/abstract.
Farhana B. Lockhat et al.; "Serum and peritoneal fluid levels of levonorgestrel in women with endometriosis who were treated with an intrauterine contraceptive device containing levonorgestrel"; Feb. 2005; Fertility and Sterility; vol. 83; No. 2; pp. 398-404; Leicester, United Kingdom.
International Searching Authority, "International Search Report and the Written Opinion of the International Searching Authority for corresponding International Patent Application PCT/US2011/066548"; dated May 1, 2012.

* cited by examiner

TREATMENT OF ENDOMETRIOSIS BY INTRAVAGINAL ADMINISTRATION OF A LOW DOSE OF A SELECTIVE PROGESTERONE RECEPTOR MODULATOR (SPRM), ANTI-PROGESTIN, OR ANTI-PROGESTATIONAL AGENT

CROSS REFERENCE TO RELATED APPLICATIONS

This application is a continuation of international application PCT/US2011/066548 filed Dec. 21, 2011, which claims the benefit of US provisional patent application No. 61/451,459 filed Mar. 10, 2011, the contents of which are incorporated by reference

TECHNICAL FIELD

The present invention relates to the treatment of endometriosis and related symptoms. More specifically, the present invention relates to the pharmacological treatment of endometriosis by intravaginal administration of low doses of a Selective Progesterone Receptor Modulator (SPRM), anti-progestin, or anti-progestational agent.

BACKGROUND

Endometriosis occurs when cells from the mucus membrane lining the uterus (endometrium) form implants that attach, grow, and function outside the uterus, generally in the pelvic region. Endometrial cells contain receptors that bind to estrogen and progesterone, which promote uterine growth and thickening. During endometriosis these cells become implanted in organs and structures outside the uterus, where these hormonal activities continue to occur, causing bleeding and scarring. Endometrial implants vary widely in size, shape, and color (accessed at http://www.endogynwiki.com/endometriosis/what-is-the-endometriosis-disease/). Endometriosis probably affects about 10 to 15% of menstruating women aged 25 to 44.[1] In North America 5.5 million women have this gynecological disorder.[2] Endometriosis is recognized as the third leading cause of gynecologic hospitalization in developed countries and a major reason for hysterectomy.[3]

Endometriosis may be found in 24% to 50% of women who experience infertility, and in more than 20% who have chronic pelvic pain.[4] In women with severe menstrual cramps, the incidence of endometriosis has been reported to be between 25% and 35%.[5] Other common symptoms include pain in the lower abdomen, pain during intercourse (dyspareunia), abdominal bloating, diarrhea, constipation, rectal bleeding, blood in the urine, and menstrual irregularities, such as heavy menstrual bleeding and spotting before menstrual periods. The symptoms usually disappear during pregnancy and after menopause (however, they may be present in menopausal women receiving estrogen replacement therapy).

Symptomatic endometriosis often requires appropriate therapy. Treatment selection is driven by the severity and type of symptoms, stage and location of the disease, a woman's age and reproductive (pregnancy) plans.

When endometriosis-induced pain is present, non-steroidal anti-inflammatory drugs (NSAIDs) may be used for temporary relief of this symptom. Inevitable dose increases (for episodes of acute incapacitating pain) or extended dosing periods (for management of chronic pain) may lead to undesirable outcomes, including gastro-intestinal and cardiovascular side effects. Some menstrual symptoms, including heavy bleeding and/or painful menstrual period, may be controlled by hormonal contraceptives. For a number of women, the treatments may not be acceptable due to known contraindications, hormone-related adverse events and/or undesirable changes in the menstrual bleeding pattern, including unpredictable intra-cyclic bleeding, irregular menstrual periods and/or development of amenorrhea.

In a majority of women, endometriosis responds to steroid hormonal therapy. The goal is to suppress production of endogenous estrogens supporting the proliferation of endometrium and the growth of endometrial implants. Increased androgen and/or progestin action also induces atrophy of the endometrium. There are medications such as gonadotropin-releasing hormone (GnRH) agonists (e.g., leuprolide acetate, goserelin acetate, and nafarelin) and androgens (e.g., danazol) which are approved for the treatment of endometriosis. However, the prolonged hypoestrogenic state which develops during treatment with these agents may also result in undesirable outcomes, including decrease in bone density, development of osteoporosis, and menopausal symptoms such as amenorrhea, hot flashes, mood swings, etc. For this reason, GnRH agonists and androgens are not recommended for long-term use. Treatment with GnRH agonists is limited by approved labeling to 6 months; danazol therapy may last up to 9 months. Following GnRH therapy, immediate add-back medications (combined or progestin-only contraceptives, combination estrogen-progestin hormone replacement regimens, bisphosphonates, etc.) may be required. Importantly, the described medications generally do not cure endometriosis; at best they temporarily reduce the size of endometrial implants while suppressing some of the symptoms.

Surgical removal of endometriosis and restoration of normal pelvic conditions is achievable via various procedures described elsewhere (see, for example, reference 1). Recurrent disease and accompanying symptoms and subsequent surgical procedures cannot be ruled out. In the most severe cases, hysterectomy with removal of the uterus and both ovaries may be the only option. Hysterectomy is a major surgical procedure used to permanently resolve the endometriosis-related symptoms. However, removal of the uterus is a radical treatment option with known undesirable characteristics, including loss of fertility, surgical morbidity and high cost.

While a number of promising candidates have been identified among selective estrogen receptor modulators (SERMs), aromatase inhibitors, anti-inflammatory drugs, and immune modulators, there is still an unmet need for an effective and safe pharmacological treatment of endometriosis.[6]

Selective progesterone receptor modulators (SPRMs) are a class of drugs acting on progesterone receptors and display progesterone antagonist or mixed agonist/antagonist activity.[7] The oldest member of this class, mifepristone, is considered as a progesterone antagonist (anti-progestin, anti-progestational agent).[11] Numerous compounds in this pharmacological class have been synthesized; some of them have been tested in clinical trials in women diagnosed with endometriosis. Efficacy and safety studies were conducted for two orally administered SPRMs: asoprisnil (Clinicaltrials.gov Identifier NCT00160420) and CDB-4124 (Proellex®; Clinicaltrials.gov Identifiers NCT00556075 and NCT00958412).

While the mechanism of action of SPRMs and anti-progestins is not completely understood, there is growing biochemical, histologic and clinical evidence that SPRMs and anti-progestins may have a critical role in controlling endometriosis growth. Studies have suggested that the compounds display direct antiproliferative effects in the endometrium in a dose-dependent fashion.[8] These effects are accompanied by an increase in progesterone, estrogen and androgen receptors and are thought to be related to progesterone antagonism and mixed progestin agonist and antagonist activity. Estrogen-dependent endometrial proliferation, mitotic and secretory activities are suppressed, and endometrial thickness and wet weight are reduced.[9] Other pharmacodynamic properties of SPRMs and anti-progestins (such as direct effects on endometrial vasculature and inhibition of ovulation) may also contribute to the development of amenorrhea[9,10], considered beneficial for women with endometriosis.

A number of clinical studies have evaluated the efficacy and safety of oral mifepristone in the treatment of gynecological disorders.[13,14,15,16,17,18] The data suggests that 10 mg/day or higher oral doses of mifepristone are effective in the reduction of uterine and fibroid volumes and related symptoms. However, at this dose, the incidence of side effects such as endometrial hyperplasia, hot flashes and elevated liver enzymes seems to be greater than desired. Two clinical programs of other SPRMs were discontinued for safety reasons. Phase III studies of oral asoprisnil were terminated due to changes in the endometrial lining of the uterus that resulted in additional invasive procedures in some patients. Phase III studies of another compound of the same class—oral CDB-4124 (Proellex®)—were suspended because of significant increases in liver enzymes. While a 5 mg/day oral mifepristone dose may be a safer alternative, its ability to reduce uterine volume and eliminate some of the fibroid-related symptoms is limited. A further oral dose reduction (2.5 mg/day) may be harder to justify due to an appreciably smaller reduction of uterine volume and a lower incidence of amenorrhea, with no noted benefits of therapy extending beyond the initial three months.[18]

Several clinical studies have investigated mifepristone in the treatment of endometriosis. In one of the trials, six normally cycling women with endometriosis were given orally 100 mg mifepristone daily for three months. Amenorrhea was reported by all study participants; all women also reported improvement in pelvic pain (notably, most patients received alternative treatment for endometriosis prior to enrollment in that study with no reduction in pain). However, no significant change in the extent of endometriosis was evident from follow-up laparoscopy.[19,20]

In another clinical trial, nine women with endometriosis received mifepristone orally, 50 mg daily for 6 months. Pelvic pain and uterine cramping improved in all patients and endometriosis regressed by 55% as evidenced by laparoscopic assessments of endometrial implants using the American Fertility Society (AFS) score. All patients exhibited amenorrhea without hypoestrogenism. Elevation of liver transaminases was observed in one subject.[21]

When the same group of researchers conducted the third clinical study in seven women with endometriosis using oral dose of mifepristone of 5 mg daily administered for 6 months, pelvic pain improved in six of seven patients and cyclic bleeding ceased in all patients; however, four women complained of irregular bleeding and mean endometriosis scores decreased by only 20%. Based on these data, the authors recommended the 50 mg mifepristone dose.[22] However, as was shown before, such a high dose may lead to the increased risk of endometrial hyperplasia and clinically significant elevations in liver enzymes (see, for example, reference 13).

Taken together, the clinical evidence indicates that the efficacy of oral mifepristone (or another SPRM, anti-progestin, or anti-progestational agent) in the treatment of gynecological disorders must be weighed against the potentially disturbing side effects associated with this medication.

Effectiveness and safety of intravaginal drug delivery is supported by a substantial body of evidence. It is established for estrogens used to treat vaginal atrophy and related symptoms[25], as well as osteoporosis and other menopausal symptoms.[26] Other examples of compounds efficacious after vaginal administration include (but are not limited to) misoprostol for cervical ripening[27], a danazol ring for the treatment of infiltrating endometriosis[28], and a progesterone gel.[29,30] The contraceptive efficacy of levonorgestrel (LNG)-containing intrauterine system, Mirena® with 20 mcg/day LNG delivery is at least comparable to that reported for the LNG-only pill delivering a 50% greater daily dose. As noted in the Mirena NDA Medical review, serum concentrations of levonorgestrel for Mirena are approximately one-tenth the serum concentration produced by an oral contraceptive containing 0.1 mg LNG and about half that produced by the Norplant® system. The local endometrial concentrations, however, are over 100 times higher in Mirena users than in users of oral contraceptives containing 0.25 mg LNG.[31] Important findings were also reported from clinical studies evaluating the systemic and local LNG concentrations and possible mechanisms of LNG delivery and action in women with endometriosis.[32] The clinical data from another study indicated the possibility of direct LNG effects mediated through estrogen and progestogen receptors on the endometrial implants themselves.[33]

SUMMARY

The present invention provides a method for effectively reducing the size of endometrial implants and/or improving other endometriosis-related symptoms without the undesirable side effects of oral medications by providing for intravaginal delivery of a Selective Progesterone Receptor Modulator (SPRM), anti-progestin, or anti-progestational agent at doses which are significantly lower than oral doses known in the art. As disclosed herein, local administration of SPRM, or anti-progestin, or anti-progestational agent can be rendered safe and efficacious if it utilizes vaginal drug delivery. Drug delivery devices useful in the method of the present invention allow for drug delivery to the affected tissues (e.g., vagina and adjacent organs, including endometrial implants). While a vaginal ring is a preferred drug delivery device in the method of the present invention, other delivery devices can be also used. Specifically, an intrauterine device (IUD) designed for insertion in women with endometriosis could be considered.

According to the present invention, the active drug (i.e., SPRM, anti-progestin, or anti-progestational agent) is delivered directly to the affected tissue(s), particularly the endometrial implants that are close to the vagina where the delivery device (e.g., vaginal ring or IUD) is placed. As specified herein, effective local concentrations of drug are achievable with doses much lower than those administered by the oral route. When used according to the method of the invention, levels of the SPRM (or anti-progestin, or anti-progestational agent) in systemic circulation are greatly reduced as compared to oral therapies, possibly below detectable limits, leading to a lower incidence of adverse events.

The intravaginal administration of mifepristone (or another SPRM, anti-progestin, or anti-progestational agent)

according to the method of the present invention substantially reduces, and possibly eliminates, first-pass hepatic metabolism. This may alleviate abnormalities in the liver function tests noted earlier. Since mifepristone has antiglucocorticoid properties (with glucocorticoid blockade reported at doses≥50 mg[24]), reduced systemic circulation of the drug ensures better control of plasma cortisol levels. Relatively high local tissue concentrations of mifepristone (or another SPRM, anti-progestin, or anti-progestational agent) achievable by the method of the present invention ensure a faster reduction in size of endometrial implants, as well as a faster improvement in related symptoms. Studies of oral mifepristone tablets suggest a treatment period ranging from 3 to 6 months.[13,14,15,16,17,18] Intravaginal delivery targeting local tissues enables a shorter duration of therapy. A shorter treatment course is expected to reduce the incidence of hyperplastic endometrial changes attributed to prolonged exposure to some anti-progestins. Better compliance (thereby avoiding missed pills by women using such a device) is also expected.

For a number of drugs delivered intravaginally, the oral route/intravaginal route ratio for the daily doses seems to be close to 10:1. The same ratio may reasonably be assumed for mifepristone (or another SPRM, anti-progestin, or anti-progestational agent).

While the exact intravaginal doses for each drug useful in the method of the present invention are going to be determined in clinical trials, the possibility of a drastic dose decrease, relative to the currently tested oral doses, with no compromise (but rather improvement) in the reduction in size of endometrial implants and in relief of related symptoms, is surprising and new. With an expected decrease in drug-related adverse events, this treatment modality may be considered as the first treatment option in the management of endometriosis.

Also surprising and new is the possibility of achieving a therapeutic effect (manifested in a reduction in size of in size of endometrial implants and in relief of related symptoms) in the absence of detectable plasma concentration levels, or in the presence of circulating levels of the drug much lower than those reported after oral administration of the same compounds.

In addition to mifepristone, the reduction in size of endometrial implants and relief of related symptoms may utilize a number of agents from a class of drugs called selective progesterone receptor modulators (SPRM), or from the class of drugs called anti-progestins, or from the class of drugs called anti-progestational agents, including, but not limited to, mifepristone, ulipristal acetate, asoprisnil, onapristone, CDB-2914, CDB-4124 and metabolites thereof. It may be noted that another SPRM, asoprisnil, at relatively low oral doses also demonstrated its ability to suppress endometrial growth and relieve endometriosis-related symptoms. It was shown that 5 mg is a minimally-effective dose for pain relief in subjects with endometriosis.[23] The exact doses of these compounds will be determined in clinical trials. Initial dose selection will be driven by a number of factors, including, but not limited to, the potency of the compound tested, the number and size of the endometrial implants and the severity of the symptoms associated with endometriosis), as well as patient characteristics (age, weight, duration of the disease, etc).

Specific dose-regimens (e.g., continuous without interruptions, or drug-administration period(s) followed by intermittent drug-free interval(s) when the drug delivery device is removed) are also going to be determined in clinical trials.

DETAILED DESCRIPTION

The embodiments disclosed herein are only examples of the many possible advantageous uses and implementations of the innovative teachings presented herein. In general, statements made in the specification of the present application do not necessarily limit any of the various claimed embodiments. Moreover, some statements may apply to some inventive features but not to others.

Definitions:

A vaginal ring (also known as an intravaginal ring) is a polymeric drug delivery device providing controlled release of drug(s) to the vagina and adjacent organs, including endometrial implants over an extended period of time.

An Intrauterine Device (also known as an IUD) is an object placed in the uterus to prevent pregnancy. In the method of the present invention, the medicated IUD is considered as a drug delivery device providing controlled release of drugs to the vagina and adjacent organs, including endometrial implants over an extended period of time.

A therapeutically effective amount of SPRM, or anti-progestin, or anti-progestational agent is defined as the amount of a drug that results in a significant (preferably, at least 15%) reduction in size of endometrial implants when compared to the pre-treatment levels.

This invention provides for intravaginal delivery of a therapeutically effective amount of Selective Progesterone Receptor Modulator (SPRM), anti-progestin, or anti-progestational agent for the reduction in size of endometrial implants and improvement in other endometriosis-related symptoms.

In the method of the present invention, the SPRM, or anti-progestin, or anti-progestational agent can be delivered using any intravaginal delivery device known in the art. Non-limiting examples of useful delivery devices include vaginal ring, intrauterine device, and vaginal tablet.

In a preferred embodiment, the drug delivery device is a vaginal ring. In another preferred embodiment, the drug delivery device is a medicated intrauterine device (IUD). In yet another embodiment, the agent can be mixed throughout the vaginal ring. In a further embodiment, the agent can be distributed uniformly throughout the vaginal ring. In another embodiment, the agent can be encapsulated in a part of the vaginal ring. In yet another embodiment, the agent can be located at the center of the vaginal ring. In a further embodiment, a membrane of the agent can be placed between an un-medicated core and a metering layer of appropriate material.

The use of vaginal drug delivery device delivering the agent directly to the affected tissues (e.g., vagina and adjacent organs, including endometrial implants) is expected to enhance the agent's efficacy in the reduction in size of the endometrial implants and improvement in related symptoms; it may also result in a shorter duration of therapy compared to other routes of drug administration.

The use of vaginal drug delivery device delivering the agent directly to the affected tissues is also expected to significantly reduce the agent's daily dose when compared to other routes of drug administration; this may result in a lower systemic drug circulation, possibly below detectable levels, and a lower incidence of drug-related adverse events.

In all embodiments, the agent is from a class of drugs called selective progesterone receptor modulators (SPRM), or from the class of drugs called anti-progestins, or from the class of drugs called anti-progestational agents. Non-limiting examples of useful agents include, e.g., mifepristone, ulipristal acetate, asoprisnil, onapristone, CDB-2914, CDB-4124, and metabolites thereof.

In one embodiment, daily agent doses useful in the method of the present invention do not exceed 1.4 mg. In another preferred embodiment, daily agent doses useful in the method of the present invention range from 50 mcg to 1 mg. In a further preferred embodiment, the agent is mifepristone with a daily drug delivery dose ranging from 100 mcg to 500 mcg. In yet another preferred embodiment, the agent is CDB-4124 with a daily drug delivery dose ranging from 150 mcg to 600 mcg. In another preferred embodiment, the agent is ulipristal acetate with a daily drug delivery dose ranging from 200 mcg to 700 mcg.

In certain embodiments, the method of the invention is used to treat females with symptomatic endometriosis. Non-limiting examples of symptoms include, e.g., infertility, pelvic pain, abdominal pain, painful intercourse (dyspareunia), abdominal bloating, diarrhea, constipation, rectal bleeding, and blood in the urine.

In certain embodiments, the method of the invention is used to treat females with non-symptomatic endometriosis (also known as asymptomatic endometriosis). In certain other embodiments, the method of the invention is used to treat females with endometriosis clinically diagnosed with menorrhagia. In certain further embodiments, the method of the invention is used to treat females with endometriosis experiencing menstrual irregularities. Non-limiting examples of menstrual irregularities include, e.g., heavy menstrual bleeding and spotting before menstrual periods.

In certain embodiments, the method of the invention is used to treat females with endometriosis clinically diagnosed with anemia. In certain other embodiments, the method of the invention is used to treat females with endometriosis clinically diagnosed with dysmenorrhea. In certain further embodiments, the method of the invention is used to treat females with endometriosis suffering from inflammatory conditions in the pelvic region. In certain other embodiments, the method of the invention is used to treat menopausal females with endometriosis. In certain further embodiments, the method of the invention is used to treat females without interruption of drug delivery with a treatment period ranging from two weeks to six months. In certain other embodiments, the method of the invention is used to treat females without interruption of drug delivery with a treatment period ranging from six months to three years.

In a preferred embodiment, the method of the invention is used to treat females without interruption of therapy with a treatment period ranging from approximately one month to approximately three months. In certain other embodiments, the method of the invention is used to treat females with the periods of drug delivery (ranging from approximately one month to approximately three months) followed by the drug-free intervals when the drug delivery device is removed. In certain further embodiments, upon administration of the agent according to the method of the invention, the amount of the agent in the female's systemic circulation is below detection levels.

The present invention is also described and demonstrated by way of the following non-limiting examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

The vaginal ring serving as a drug delivery device comprises a supporting ring free of active drug. The next (second) layer contains medication selected for treatment of endometrial implants (selective progesterone receptor modulator, or anti-progestin, or anti-progestational agent). This layer is coated with the third, drug-free layer. Detailed description of such vaginal ring and suitable manufacturing methods can be found in U.S. Pat. No. 4,822,616.

Per U.S. Pat. No. 4,822,616, the supporting ring is made from a physiologically acceptable synthetic resin, such as, e.g., polyethylene, RTV silicone elastomers, LTV silicone elastomers, polyamides and polytetrafluoroethylene. The second layer with active medication comprises a pharmaceutically acceptable resin from which the drug is released. A preferred embodiment consists of the combination of drug and LTV silicone elastomer with a composition also described in the patent. Any LTV silicone elastomer is used in the third layer. The proposed vaginal ring ensures release of the active drug within the limits of the dosage required for the desired reduction in size of endometrial implants.

In one embodiment, the second layer is medicated with mifepristone in an amount adequate to release the drug in a rate of 250-300 mcg/day. In another embodiment, the second layer is medicated with CDB-4124 in an amount adequate to release the drug in a rate of 300-400 mcg/day. In yet another embodiment, the second layer is medicated with ulipristal acetate in an amount adequate to release the drug in a rate of 300-500 mcg/day.

In all described embodiments, the treatment is continuous without interruption. A preferred duration of therapy (following insertion of the ring) ranges from approximately one month to approximately three months.

Example 2

The vaginal ring serving as a drug delivery device comprises active drug selected for treatment of excessive menstrual blood loss (tranexamic acid or another antifibrinolytic or hemostatic agent) and a delivery module. Delivery module comprises (a) reservoir for storing the active drug, (b) a rate controller or wall that is formed of styrene-butadiene copolymer that maintains the prescribed rate of drug release throughout the life of system, (c) energy source or the concentration of active drug in reservoir that provides the driving means for transferring the active drug from a higher amount in reservoir to the rate controller, (d) an inner mass transfer conductor for housing the active drug in reservoir, and (e) a portal that provides the exit from the drug delivery module to the tissues. Detailed description of such vaginal ring and its manufacturing process can be found, for example, in U.S. Pat. No. 4,250,611.

In one embodiment, the delivery module of the vaginal ring contains mifepristone in an amount supporting the drug release at a rate of 250-300 mcg/day. In another embodiment, the delivery module of the vaginal ring contains CDB-4124 in an amount supporting the drug release at a rate of 300-400 mcg/day. In yet another embodiment, the delivery module of the vaginal ring contains ulipristal acetate in an amount supporting the drug release at a rate of 300-500 mcg/day.

In all described embodiments, the treatment is continuous without interruption. A preferred duration of therapy (following insertion of the ring) ranges from approximately one month to approximately four months.

Example 3

The vaginal ring serving as a drug delivery device is a ring-shaped solid carrier made of silicone rubber (polysiloxane) or other suitable material. The ring has a homogenous design with an active drug dispersed in the carrier. Detailed description of such vaginal ring can be found, for example, in U.S. Pat. No. 5,869,081.

Per U.S. Pat. No. 5,869,081, the vaginal ring provides sustained release of the medication and results in low circulatory levels of the drug, while concentrating its biological effect on a regional level.

In one embodiment, the carrier contains mifepristone in an amount supporting the drug release at a rate of 250-300 mcg/day. In another embodiment, the carrier contains CDB-4124 in an amount supporting the drug release at a rate of 300-400 mcg/day. In yet another embodiment, the carrier contains ulipristal acetate in an amount supporting the drug release at a rate of 300-500 mcg/day.

In all described embodiments, the treatment is continuous without interruption. A preferred duration of therapy (following insertion of the ring) ranges from approximately two weeks to approximately one month.

Example 4

The medicated intrauterine device (IUD) serving as a drug delivery device is inserted into the uterus for a predetermined time period. The device comprises a body of the device in combination with an external surface contacting the uterus. The external surface is medicated and provides controlled drug release. Detailed description of such IUD can be found in U.S. Pat. No. 4,359,046.

In one embodiment, the IUD is medicated with mifepristone in an amount supporting the drug's release at a rate of 200-250 mcg/day. In another embodiment, the carrier contains CDB-4124 in an amount supporting the drug release at a rate of 250-300 mcg/day. In yet another embodiment, the carrier contains ulipristal acetate in an amount supporting the drug release at a rate of 250-300 mcg/day.

Contraceptive action of the IUD is considered as optional. In all described embodiments, the treatment is continuous without interruption. A preferred duration of therapy (following insertion of the IUD) is up to three years.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

REFERENCES

[1] Clement P B: Pathology of endometriosis. Pathol Annu 25: 245-295, 1990

[2] The official site of Lupron Depot® Understanding Endometriosis.

[3] Garai J., et al. Endometriosis: harmful survival of an ectopic tissue. Frontiers in Bioscience 11, 595-619, Jan. 1, 2006

[4] Endometriosis. A Guide for Patients. American Society for Reproductive Medicine. Patient information series. 2007 (reference on file)

[5] Babaknia A. Endometriosis The 90's Outlook. (Endometriosis FAQ).

[6] Fedele L., Berlanda N. Emerging drugs for endometriosis. Expert Opin. Emerg Drugs. 2004 May; 9(1):167-77.

[7] Spitz I M., Mifepristone: where do we come from and where are we going? Clinical development over a quarter of a century. Contraception. Corrected Proof. 1 Feb. 2010.

[8] Chabbert-Buffet N. et al. Selective progesterone receptor modulators and progesterone antagonists: mechanisms of action and clinical applications. Hum Reprod Update 11:293-307; 2005.

[9] Spitz I M., Mifepristone: where do we come from and where are we going? Clinical development over a quarter of a century. Contraception. Corrected Proof. 1 Feb. 2010

[10] Steinauer, J, Pritts, E A, Jackson, R, Jacoby A F. Systematic review of mifepristone for the treatment of uterine leiomyomata. Obstet Gynecol 2004; 103:1331.

[11] Spitz I M. Pharmacology and mechanisms of action of progesterone receptor antagonists and selective progesterone receptor modulators. UpToDate. Online 18.2, May 2010.

[12] Mifepristone. Wikipedia.

[13] Steinauer, J, Pritts, E A, Jackson, R, Jacoby A F. Systematic review of mifepristone for the treatment of uterine leiomyomata. Obstet Gynecol 2004; 103:1331.

[14] Eisinger S H., et al. Twelve-month safety and efficacy of low-dose mifepristone for uterine myomas. J Minim Invasive Gynecol 2005; 12:227.

[15] Gommier B, Magning G. Mifepristone for treatment of myomas [meeting abstract]. Third Symposium. Misoprostol and mifepristone in obstetrics and gynecology. Valencia, Spain, Oct. 4-5, 2007).

[16] Fiscella K, et al. Effect of mifepristone for symptomatic leiomyomata on quality of life and uterine size: a randomized controlled trial. Obstet Gynecol 2006; 108:1381-7.

[17] Esteve C J L, et al. Mifepristone for the treatment of uterine leiomyomas: a randomized controlled trial. Obstet Gynecol 2008; 112:1029-36.

[18] Eisinger, S H, et al. Open-label study of ultra low-dose mifepristone for the treatment of uterine leiomyomata. Eur J Obstet Gynecol Reprod Biol 2009, Oct., 1; 146(2): 215-8.

[19] Kettel L M, et al. Endocrine responses to long-term administration of the antiprogesterone RU486 in patients with pelvic endometriosis. Fertil Steril 1991; 56:402-7.

[20] Donaldson M S. Et al. Clinical Applications of Mifepristone (RU486) and Other Antiprogestins. Assessing the Science and Recommending a Research Agenda. National Academy Press, Washington, D.C., 1993.

[21] Kettel L M, et al. Treatment of endometriosis with the antiprogesterone mifepristone (RU486). Fertil Steril 1996; 65:23-8.

[22] Kettel L M, et al. Preliminary report on the treatment of endometriosis with low-dose mifepristone (RU 486). Am J Obstet Gynecol 1998; 178:1151-6.

[23] Huang H Y. Medical Treatment of Endometriosis. Chang Gung Med J 2008; 31:431-40)

[24] Fiscella K. Use of antiprogestins for treatment of uterine fibroids: clinical trials (presentation). Advances in Uterine Leiomyoma Research. 2nd NIH International Congress. Feb. 24-25, 2005. Bethesda Md. (reference on file).

[25] Kingsberg S A., et al. Treating dyspareunia caused by vaginal atrophy: a review of treatment options using vaginal estrogen therapy. International Journal of Women's Health. August 2009, Volume 2009:1 Pages 105-111

[26] Ballagh S A. Vaginal Ring Hormone Delivery Systems in Contraception and Menopause. CLINICAL OBSTETRICS AND GYNECOLOGY/VOLUME 44/NUMBER 1/MARCH 2001

[27] Iyer V., et al. Vaginal drug delivery. ExpressPharma, 1-15 Jul. 2008

[28] Igarashi M. Novel vaginal danazol ring therapy for pelvic endometriosis, in particular deeply infiltrating endometriosis. Hum Reprod. 1998 July; 13(7):1952-6.

[29] Ficicioglu C. et al. High local endometrial effect of vaginal progesterone gel. Gynecological Endocrinology, Volume 18, Issue 5 May 2004, pages 240-243.

[30] Kuhl H. Pharmacology of estrogens and progestogens: influence of different routes of administration. Climacteric 2005; 8(Suppl 1)3-63.

[31] Center for Drug Evaluation and Research. Application Number 21-225. Mirena® NDA Medical review

[32] Nilsson C G, et al. Tissue concentration of levonorgestrel in women using a levonorgestrel-releasing IUD. Clin Endocrinol 1982; 17:529-36.

[33] Lockhat F B, Emembolu J E, Konje J C. Serum and peritoneal fluid levels of levonorgestrel in women with endometriosis who were treated with an intrauterine contraceptive device containing levonorgestrel. Fertil Steril 2005; 83: 398-404.

What is claimed is:

1. A method of treating one or more endometrial implants comprising:
    administering intravaginally to a female in need thereof a delivery device comprising a therapeutically effective amount of a single active agent, wherein the single active agent is selected from the group consisting of mifepristone and metabolites thereof and the device is positioned in the vagina proximate to the implants to be treated, wherein the daily dose of the single active agent does not exceed 500 mcg.

2. The method of claim 1, wherein the delivery device is any one of: a vaginal ring, a medicated intrauterine device (IUD), and a vaginal tablet.

3. The method of claim 2, wherein the single active agent contained in the vaginal ring is any one of the following forms: mixed throughout the vaginal ring, distributed uniformly throughout the vaginal ring; encapsulated in a part of the vaginal ring, located at the center of the vaginal ring, and placed between an un-medicated core and a metering layer of the vaginal ring.

4. The method of claim 1, wherein the single active agent is mifepristone with the daily dose ranging from 100 mcg to 400 mcg.

5. The method of claim 1, wherein the single active agent is administered: without interruption of drug delivery with duration of treatment period ranging from two weeks to six months, without interruption of drug delivery with duration of treatment period ranging from six months to three years.

6. The method of claim 1, wherein the single active agent is administered in at least two periods of drug delivery ranging from one month to three months, separated by drug-free intervals when the drug delivery device is removed.

7. A method of treating one or more endometrial implants comprising:
    administering intravaginally to a female in need thereof a delivery device comprising a therapeutically effective amount of a single active agent, wherein the single active agent is selected from the group consisting of mifepristone and metabolites thereof, and the device is positioned in the vagina proximate to the implants to be treated, wherein the daily dose of the single active agent does not exceed 500 mcg,
    wherein the female has non-symptomatic or symptomatic endometriosis, wherein endometriosis symptom comprises at least one of: infertility, pelvic pain, abdominal pain, painful intercourse, abdominal bloating, diarrhea, constipation, rectal bleeding, blood in the urine, heavy menstrual bleeding, spotting before menstrual periods, menorrhagia, anemia, dysmenorrhea, and inflammation in the pelvic region.

8. A method of treating one or more endometrial implants comprising:
    administering intravaginally to a female in need thereof a delivery device comprising a therapeutically effective amount of a single active agent, wherein the single active agent is selected from the group consisting of mifepristone and metabolites thereof, and the device is positioned in the vagina proximate to the implants to be treated, wherein the daily dose of the single active agent does not exceed 500 mcg
    wherein upon administration of the single active agent the amount of the active agent in the female's systemic circulation is below measurable drug concentration levels.

* * * * *